(12) United States Patent
Yamazaki

(10) Patent No.: US 10,564,110 B2
(45) Date of Patent: Feb. 18, 2020

(54) PRINTING RESULT INSPECTION APPARATUS AND METHOD

(71) Applicant: FUJIFILM Corporation, Tokyo (JP)

(72) Inventor: Yoshirou Yamazaki, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/124,080

(22) Filed: Sep. 6, 2018

(65) Prior Publication Data

US 2019/0003985 A1 Jan. 3, 2019

Related U.S. Application Data

(63) Continuation of application No. PCT/JP2017/007872, filed on Feb. 28, 2017.

(30) Foreign Application Priority Data

Mar. 9, 2016 (JP) .................. 2016-045963

(51) Int. Cl.
*B41J 2/045* (2006.01)
*G01N 21/892* (2006.01)
(Continued)

(52) U.S. Cl.
CPC ....... *G01N 21/892* (2013.01); *B41F 33/0036* (2013.01); *B41F 33/16* (2013.01);
(Continued)

(58) Field of Classification Search
CPC ........ B41J 2/0451; B41J 2/04558; B41J 2/20; B41J 2/0456; B41J 2/195; B41J 2/2132; G01N 21/892
See application file for complete search history.

(56) References Cited

U.S. PATENT DOCUMENTS 9,088,673 B2 7/2015 Banner et al.
2008/0252676 A1* 10/2008 Yasutani et al. ................ 347/16
(Continued)

FOREIGN PATENT DOCUMENTS

DE 4023314 A1 1/1992
DE 19917899 A1 11/2000
(Continued)

OTHER PUBLICATIONS

International Search Report issued in PCT/JP2017/007872; dated May 9, 2017.
(Continued)

*Primary Examiner* — Juanita D Jackson
(74) *Attorney, Agent, or Firm* — Studebaker & Brackett PC

(57) ABSTRACT

Provided are a printing result inspection apparatus, a method, and a program capable of determining a printing defect caused by a printing step and a printing paper defect caused by printing paper by reading the printing paper once. A defect determination unit determines whether defected regions extracted from a non-image region are the printing defect or the printing paper defect based on a density change amount and a color, and an image feature amount of a defected region determined as the printing paper defect in the non-image region is stored in paper defect information and is accumulated in a paper defect information storage unit. Next, the defect determination unit determines whether defected regions extracted from image regions are the printing defect or the printing paper defect based on the paper defect information.

13 Claims, 6 Drawing Sheets

(51) Int. Cl.

| | | |
|---|---|---|
| *B41J 2/20* | (2006.01) | |
| *G06T 7/00* | (2017.01) | |
| *H04N 1/60* | (2006.01) | |
| *B41F 33/00* | (2006.01) | |
| *G01N 21/89* | (2006.01) | |
| *B41J 2/165* | (2006.01) | |
| *G06T 1/00* | (2006.01) | |
| *G01N 21/956* | (2006.01) | |
| *B41F 33/16* | (2006.01) | |
| *B41J 2/21* | (2006.01) | |
| *G01N 21/88* | (2006.01) | |

(52) U.S. Cl.
CPC ......... *B41J 2/0451* (2013.01); *B41J 2/04558* (2013.01); *B41J 2/16579* (2013.01); *B41J 2/20* (2013.01); *B41J 2/2142* (2013.01); *G01N 21/8903* (2013.01); *G01N 21/95607* (2013.01); *G06T 1/00* (2013.01); *G06T 7/001* (2013.01); *H04N 1/6097* (2013.01); *G01N 2021/8854* (2013.01); *G01N 2021/8917* (2013.01); *G06T 2207/10024* (2013.01); *G06T 2207/30144* (2013.01)

(56) References Cited

U.S. PATENT DOCUMENTS

| | | | |
|---|---|---|---|
| 2014/0292888 A1* | 10/2014 | Terada | 347/19 |
| 2015/0273911 A1* | 10/2015 | Derluth | B41J 2/04558 |

FOREIGN PATENT DOCUMENTS

| | | |
|---|---|---|
| JP | H08-221633 A | 8/1996 |
| JP | H10-208055 A | 8/1998 |
| JP | 2005-092826 A | 4/2005 |
| JP | 2005-205853 A | 8/2005 |
| JP | 2006-145261 A | 6/2006 |
| JP | 2007-104201 A | 4/2007 |
| JP | 3156399 U | 12/2009 |
| JP | 2013-208838 A | 10/2013 |
| JP | 2015-223717 A | 12/2015 |
| JP | 2017-032507 A | 2/2017 |

OTHER PUBLICATIONS

International Preliminary Report on Patentability and Written Opinion issued in PCT/JP2017/007872; dated Sep. 11, 2018.
Extended European Search Report issued by the European Patent Office dated Jan. 24, 2019, which corresponds to EP17763016.7-1014 and is related to U.S. Appl. No. 16/124,080.

* cited by examiner

PRINTING RESULT INSPECTION APPARATUS AND METHOD

CROSS-REFERENCE TO RELATED APPLICATIONS

The present application is a Continuation of PCT International Application No. PCT/JP2017/007872 filed on Feb. 28, 2017 claiming priority under 35 U.S.C § 119(a) to Japanese Patent Application No. 2016-045963 filed on Mar. 9, 2016. Each of the above applications is hereby expressly incorporated by reference, in their entirety, into the present application.

BACKGROUND OF THE INVENTION

1. Field of the Invention

The present invention relates to a printing result inspection apparatus and a method thereof, and relates particularly to the printing result inspection apparatus and the method thereof that acquire an image on printing paper to detect a defect.

2. Description of the Related Art

JP2006-145261A discloses a plate inspection apparatus that compares reference image data prepared in advance with read image data obtained by imaging a printing plate to inspect whether the printing plate is appropriately created. The plate inspection apparatus according to JP2006-145261A refers to data relating to a color range present in a normal printing plate and the reference image data so as to identify an image region, a defective exposure region, a scratched region, a printing blur region, and dust.

JP2005-205853A discloses a printing result inspection apparatus that inspects a printing result by an image forming apparatus that prints an image on paper based on original document image data. The printing result inspection apparatus according to JP2005-205853A reads paper surfaces of the paper before and after the printing by the image forming apparatus and respectively acquires image data before the printing and image data after the printing so as to determine whether the printing result is good or not based on the image data before the printing and the image data after the printing.

JP2013-208838A discloses a printed matter inspection apparatus that inspects a printed matter printed by a printing unit in which an ink jet line head that covers the entire printing region in the width direction of a printing medium is disposed along a transportation path of the printing medium for each color of color printing. The printed matter inspection apparatus according to JP2013-208838A detects a place where a density value of pickup image data is higher than a density value of reference printing data as a flaw of "dirt", detects a flaw having a feature of being comparatively large and extending in an elongated shape in a transportation direction of the printing medium as the flaw of "ink dripping", detects other flaws as the flaw of "paper dirt", and detects a place where a density integrating accumulate value of the reference printing data is higher than a density integrating accumulate value of the pickup image data as the flaw of "nozzle missing".

SUMMARY OF THE INVENTION

In general, in a step of manufacturing printing paper (in particular, step of manufacturing of low cost printing paper such as recycled paper), since a foreign substance (for example, dust, ink adhering to used paper, or adhesive matter (glue)) included in the raw material (pulp and the like) of the printing paper cannot be removed sufficiently, the foreign substance may remain on the printing paper. Therefore, in a case where an image or the like is printed on the printing paper, not only a printing defect caused by a printing step (defect caused by ink used in printing, ink dripping, or the like) but also a printing paper defect caused by the printing paper (defect caused by the foreign substance, paper unevenness, or the like) may occur. However, in the inspection of the printing result in the related art, it is difficult to separately detect the printing defect and the printing paper defect from an image obtained by imaging the printing paper after printing.

JP2006-145261A relates to the plate inspection apparatus and is not for detecting the printing paper defect and the printing defect on the printing paper after the image or the like is printed. The plate inspection apparatus according to JP2006-145261A is for identifying the defective exposure region having density higher than the image region due to defective exposure, the scratched region having low density due to exposure of a base layer caused by a damaged image forming layer, the printing blur region having density lower than the image region due to a thicker dot shape than a desired shape caused by inappropriate focusing at the time of exposure of the printing plate, and the dust that deviates from a color range of the image region using a fact that the printing plate which is colored before exposure becomes white after the exposure (paragraphs [0016] to [0021]). Therefore, the technique according to JP2006-145261A cannot be employed in the detection of the printing paper defect caused by the printing paper.

The printing result inspection apparatus according to JP2005-205853A includes two reading units of a pre-printing reading unit and a post-printing reading unit in order to read the paper surfaces of the paper before and after the printing by the image forming apparatus (paragraph [0015] and the like). Therefore, according to JP2005-205853A, there is a problem that the apparatus becomes large and complicated, and a cost for manufacturing and operating the apparatus increases.

The printed matter inspection apparatus according to JP2013-208838A is for determining "ink dripping" and "paper dirt" based on a morphological feature of the flaw of "dirt" (paragraph and the like), and cannot detect the printing paper defect depending on a type of the printing paper.

The present invention is made in view of such circumstances, and an object of the invention is to provide a printing result inspection apparatus and a method thereof capable of determining the printing defect caused by the printing step and the printing paper defect caused by the printing paper by reading the printing paper once.

In order to solve the problems described above, a printing result inspection apparatus according to a first embodiment of the present invention comprises inspection image data acquisition means for acquiring inspection image data obtained by imaging printing paper after printing, defected region detection means for comparing the inspection image data with reference image data including an image printed on the printing paper to detect a defected region from the inspection image data, first defect determination means for determining whether a defected region included in a non-image region is a printing defect caused by a printing step or a printing paper defect caused by printing paper based on a density change amount and a color of the defected region included in the non-image region where the image on the printing paper is not printed among defected regions detected by the defected region detection means, storage means for storing image feature amount information indicating an image feature amount of a defected region determined as the printing paper defect by the first defect determination means, and second defect determination means for determining whether a defected region included in an image region excluding the non-image region on the printing paper among the defected regions detected by the defected region detection means is the printing defect or the printing paper defect based on the image feature amount information of the defected region determined as the printing paper defect, and a density change amount and a color of the defected region included in the image region.

According to the first embodiment, it is possible to determine the printing defect caused by the printing step and the printing paper defect caused by the printing paper by reading the printing paper once after the printing by performing the determination using the features of the density change amount and the color of the defected region in the non-image region, and by performing the determination of the defected region in the image region using the result.

In the printing result inspection apparatus according to a second embodiment of the present invention, the storage means stores image feature amount information indicating an image feature amount of a defected region determined as the printing paper defect by the second defect determination means in the first embodiment.

In the printing result inspection apparatus according to a third embodiment of the present invention, the storage means stores paper specification information that specifies the printing paper in correlation with the image feature amount information, and in a case of inspecting printing paper having the same paper specification information as paper specification information recorded in the storage means, the first defect determination means and the second defect determination means determine whether the defected region is the printing defect or the printing paper defect using the image feature amount information correlated with the paper specification information in the first or second embodiment.

According to the third embodiment, it is possible to use the image feature amount information prepared in advance in determining the printing defects and the printing paper defects on pieces of printing paper of the same lot. Accordingly, it is possible to reflect the inspection results of the pieces of printing paper of the same lot in determining the printing defect and the printing paper defect.

In the printing result inspection apparatus according to a fourth embodiment of the present invention, the storage means stores image feature amount information indicating an image feature amount of the defected region determined as the printing defect by the first defect determination means, and the second defect determination means determines whether the defected region included in the image region excluding the non-image region on the printing paper is the printing defect or the printing paper defect based on the image feature amount information of the defected region determined as the printing paper defect, the image feature amount information of the defected region determined as the printing defect, and the density change amount and the color of the defected region included in the image region in any of the first to third embodiments.

According to the fourth embodiment, since the image feature amount information of the printing defect can be used in addition to the image feature amount information of the printing paper defect, it is possible to perform the determination more adapted to unique features of the printing paper and a printing apparatus.

In the printing result inspection apparatus according to a fifth embodiment of the present invention, in a case where the density change amount measured for the defected region is equal to or larger than a first threshold value, the first defect determination means determines that the defected region is the printing defect in any of the first to fourth embodiments.

According to the fifth embodiment, it is possible to determine whether the defected region is the printing paper defect based on the density change amount of the defected region.

In the printing result inspection apparatus according to a sixth embodiment of the present invention, in the case where the density change amount measured for the defected region is equal to or larger than the first threshold value, the first defect determination means determines that the defected region is the printing defect, and in a case where the density change amount measured for the defected region is equal to or less than a second threshold value which is smaller than the first threshold value, the first defect determination means determines that the defected region is the printing paper defect in the fifth embodiment.

According to the sixth embodiment, it is possible to determine whether the defected region is the printing defect or the printing paper defect based on the density change amount of the defected region.

In the printing result inspection apparatus according to a seventh embodiment of the present invention, in a case where a color of an ink used for printing the printing paper and a color of the defected region are compared with each other, and the color of the ink and the color of the defected region are determined to be the same, the first defect determination means determines that the defected region is the printing defect in any of the first to sixth embodiments.

In the printing result inspection apparatus according to an eighth embodiment of the present invention, the first defect determination means determines whether the defected region is the printing defect based on at least one of a color difference, a chroma difference, or a color tone difference between the color of the ink used for printing the printing paper and the color of the defected region in the seventh embodiment.

According to the seventh and eighth embodiments, it is possible to determine whether the defected region is the printing defect based on the color of the defected region and the color of the ink.

In the printing result inspection apparatus according to a ninth embodiment of the present invention, in a case where there is a defected region which is not possible to be determined as either the printing defect or the printing paper defect, the first defect determination means calculates a comprehensive evaluation value based on a density change amount and a color of the defected region and determines whether the defected region is the printing defect or the printing paper defect based on the comprehensive evaluation value in any of the first to eighth embodiments.

In the printing result inspection apparatus according to a tenth embodiment of the present invention, the first defect determination means calculates the comprehensive evaluation value based on a shape of the defected region in the ninth embodiment.

According to the tenth embodiment, it is possible to more reliably perform the determination of the defected region by considering the shape of the defected region in addition to the density change amount and the color.

In the printing result inspection apparatus according to an eleventh embodiment of the present invention, the reference image data includes information indicating a color of the printing paper, and the defected region detection means calculates a difference between the inspection image data and the reference image data and the color of the printing paper, and acquires difference image data to detect the defected region from the inspection image data in any of the first to tenth embodiments.

A method of inspecting a printing result according to a twelfth embodiment of the present invention comprises an inspection image data acquisition step of acquiring inspection image data obtained by imaging printing paper after printing, a defected region detection step of comparing the inspection image data with reference image data including an image printed on the printing paper to detect a defected region from the inspection image data, a first defect determination step of determining whether a defected region included in a non-image region is a printing defect caused by a printing step or a printing paper defect caused by printing paper based on a density change amount and a color of the defected region included in the non-image region where the image on the printing paper is not printed among defected regions detected in the defected region detection step, a storage step of storing image feature amount information indicating an image feature amount of a defected region determined as the printing paper defect in the first defect determination step in storage means, and a second defect determination step of determining whether a defected region included in an image region excluding the non-image region on the printing paper among the defected regions detected in the defected region detection step is the printing defect or the printing paper defect based on the image feature amount information of the defected region determined as the printing paper defect, and a density change amount and a color of the defected region included in the image region.

A printing result inspection program according to a thirteenth embodiment of the present invention causes a computer to realize an inspection image data acquisition function of acquiring inspection image data obtained by imaging printing paper after printing, a defected region detection function of comparing the inspection image data with reference image data including an image printed on the printing paper to detect a defected region from the inspection image data, a first defect determination function of determining whether a defected region included in a non-image region is a printing defect caused by a printing step or a printing paper defect caused by printing paper based on a density change amount and a color of the defected region included in the non-image region where the image on the printing paper is not printed among defected regions detected by the defected region detection function, a storage function of storing image feature amount information indicating an image feature amount of the defected region determined as a printing paper defect by the first defect determination function, and a second defect determination function of determining whether a defected region included in an image region excluding the non-image region on the printing paper among the defected regions detected by the defected region detection function is the printing defect or the printing paper defect based on the image feature amount information of the defected region determined as the printing paper defect, and a density change amount and a color of the defected region included in the image region.

According to the present invention, it is possible to determine the printing defect caused by the printing step and the printing paper defect caused by the printing paper by reading the printing paper once after the printing.

DESCRIPTION OF THE PREFERRED EMBODIMENTS

Hereinafter, an embodiment of a printing result inspection apparatus and a method thereof according to the present invention will be described with reference to accompanying drawings.

[Configuration of Printing Result Inspection Apparatus]

Figure 1:
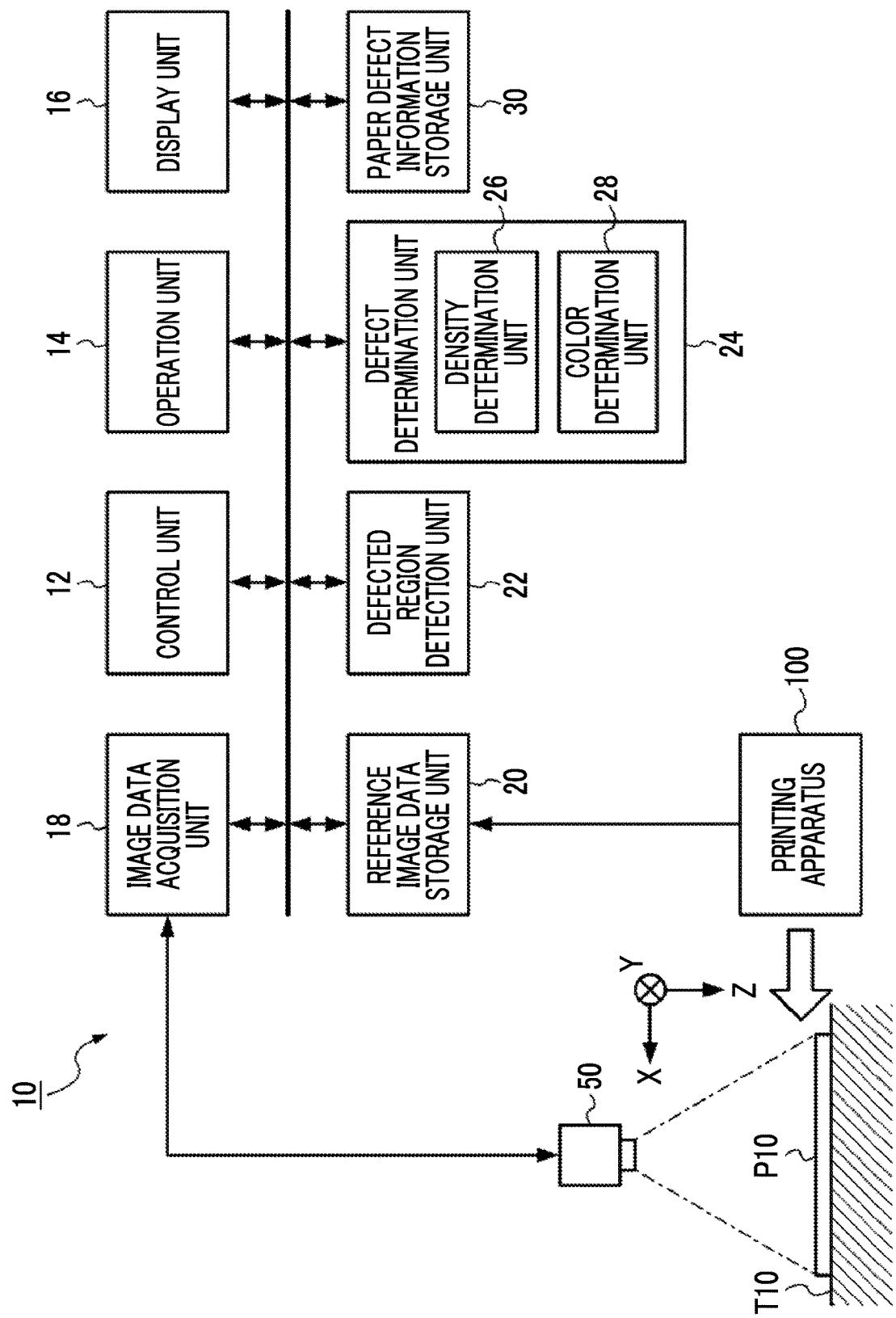
FIG. 1 is a block diagram showing a printing result inspection apparatus according to an embodiment of the present invention.

FIG. 1 is a block diagram showing the printing result inspection apparatus according to the embodiment of the present invention. In the following description, a transportation direction of printing paper P10 is set as the X direction, a direction orthogonal to the X direction in a plane of the printing paper P10 is set as the Y direction, and a direction orthogonal to the printing paper P10 is set as the Z direction.

A printing result inspection apparatus 10 according to the embodiment images the printing paper P10 on which an image or the like is printed by a printing apparatus 100 with a camera 50 and extracts a defected region including a defect from a pickup image of the printing paper P10 to determine a printing defect caused by a printing step (defect caused by ink used in printing, ink dripping, or the like) and a printing paper defect caused by printing paper (defect caused by the foreign substance, paper unevenness, or the like). As shown in FIG. 1, the printing result inspection apparatus 10 according to the embodiment includes a control unit 12, an operation unit 14, a display unit 16, an image data acquisition unit 18, a reference image data storage unit 20, a defected region detection unit 22, a defect determination unit 24, and a paper defect information storage unit 30.

The control unit 12 includes a central processing unit (CPU) that controls an operation of each of units and the like of the printing result inspection apparatus 10 and a read only memory (ROM) for storing data including a control program used by the CPU. The control unit 12 accepts operation input from an operator through the operation unit 14 and transmits a control signal according to the operation input to each of units and the like of the printing result inspection apparatus 10 to control the operation of each of units and the like.

The operation unit 14 is an input apparatus that accepts the operation input from the operator and includes a keyboard for character input and a pointing apparatus (mouse, trackball, or the like) for operating a pointer, an icon, and the like displayed on the display unit 16. A touch panel may be also provided on a surface of the display unit 16 as the operation unit 14 instead of the means described above or in addition to the means described above.

The display unit 16 is an apparatus for displaying an image. For example, a liquid crystal monitor may be used as the display unit 16.

The image data acquisition unit 18 (inspection image data acquisition means) acquires an image of the printing paper P10 imaged by the camera 50 (for example, charge coupled device (CCD) camera). In the embodiment, the camera 50 is disposed on a transportation path T10 for discharging the printing paper P10 outside the printing apparatus 100 after the image or the like is printed on the printing paper P10 by the printing apparatus 100 (for example, ink jet printer), and sequentially images each part of the printing paper P10 during transportation. The image data acquisition unit 18 acquires an image of each part of the printing paper P10 imaged by the camera 50 to create an image of the entire printing paper P10 (hereinafter, referred to as inspection image data IMG1).

The reference image data storage unit 20 is storage means that stores the original data of the image printed on the printing paper P10. The reference image data storage unit 20 acquires image data (hereinafter, referred to as reference image data REF1) used for forming the image for each printing paper P10 from the printing apparatus 100.

Communication means between the image data acquisition unit 18 of the printing result inspection apparatus 10 and the camera 50 and communication means between the reference image data storage unit 20 and the printing apparatus 100 are not particularly limited. For example, a network such as a local area network (LAN), a wide area network (WAN), or an Internet connection, a universal serial bus (USB) cable, or Bluetooth (registered trademark) may be used as the communication means.

In the embodiment, the printing result inspection apparatus 10, the camera 50, and the printing apparatus 100 are separate apparatuses, but the present invention is not limited thereto. For example, the printing result inspection apparatus 10 may be included in the printing apparatus 100. In the case, a step of acquiring the reference image data REF1 from the printing apparatus 100 by the printing result inspection apparatus 10 is unnecessary. The camera 50 may be included in the printing result inspection apparatus 10 or the printing apparatus 100. The camera 50 may be disposed, for example, on the transportation path (discharge path) of the printing paper P10 in the printing apparatus 100. In the case where the camera 50 is included in the printing result inspection apparatus 10, a step of acquiring the inspection image data IMG1 by the image data acquisition unit 18 is unnecessary.

The defected region detection unit 22 (defected region detection means) compares the inspection image data IMG1 with the reference image data REF1 to detect the defected region. The defected region detection unit 22 acquires difference image data IMG2 between the inspection image data IMG1 and the reference image data REF1, and detects a region having a difference between the inspection image data IMG1 and the reference image data REF1 (for example, region having a difference in color or image shape, or region where the difference in color or image shape is equal to or larger than a threshold value) as the defected region using the difference image data IMG2.

The defect determination unit 24 (first defect determination means, second defect determination means) determines whether the defected region detected by the defected region detection unit 22 is the printing defect or the printing paper defect.

The paper defect information storage unit 30 (storage means) stores a determination result of the defected region by the defect determination unit 24 and information on an image feature amount of each defected region. For example, an apparatus including a magnetic disk such as a hard disk drive (HDD), an apparatus including a flash memory such as an embedded multi media card (eMMC) or a solid state drive (SSD), or the like may be used as the paper defect information storage unit 30.

[Method of Detecting Defected Region]

Figure 2:
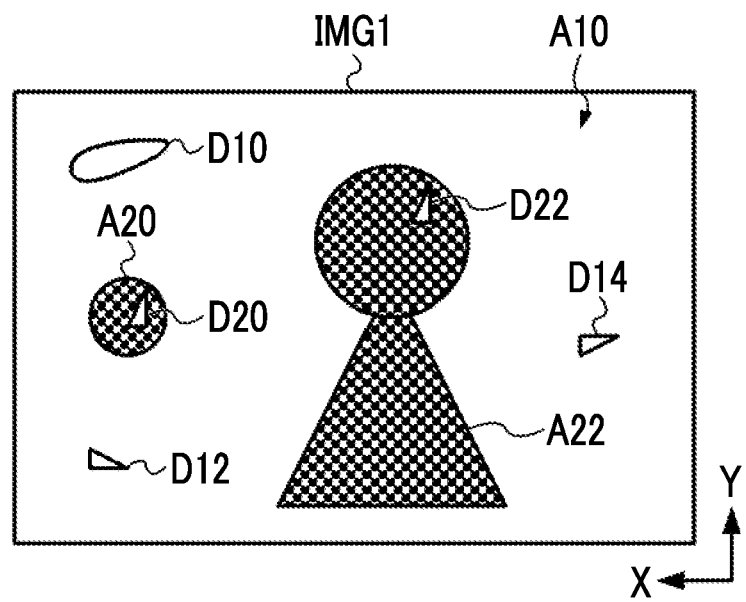
FIG. 2 is a diagram showing an example of inspection image data.
Figure 3:
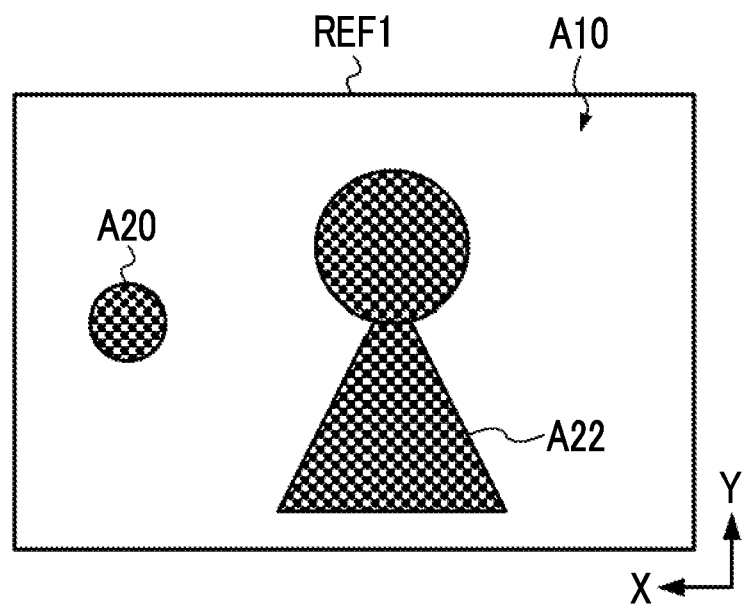
FIG. 3 is a diagram showing an example of reference image data.
Figure 4:
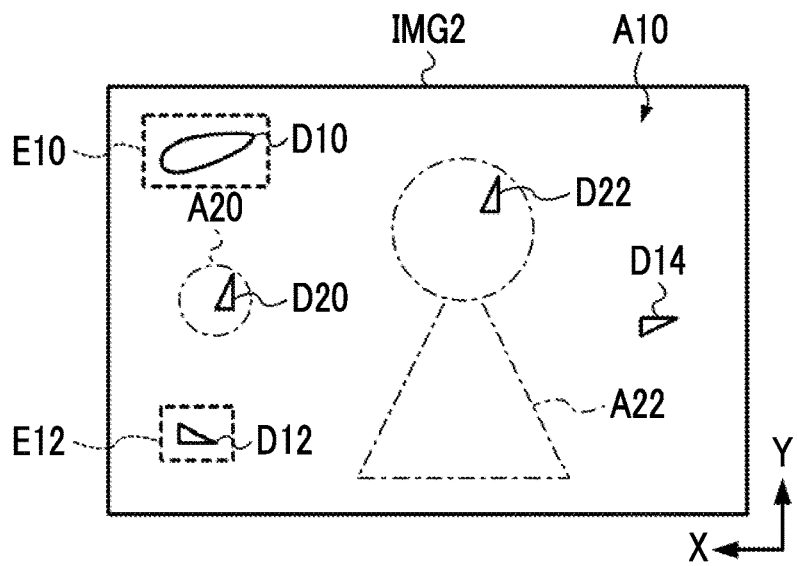
FIG. 4 is a diagram showing an example of difference image data.

Here, a method of detecting the defected region will be described. FIGS. 2 to 4 are diagrams respectively showing examples of inspection image data, reference image data, and difference image data.

In the example shown in FIG. 3, the reference image data REF1 includes a non-image region A10, image regions A20 and A22, and information relating to a color of ink used for each pixel (for example, ink colors of CMYK (cyan, magenta, yellow, black)). The image regions A20 and A22 are regions where the ink is dropped by the printing apparatus 100 to form the images, and the non-image region A10 is a region where the image is not formed. The image region and the non-image region are determined, for example, based on whether an area of a region where the ink is dropped per unit area (density of a region where an image is formed) is equal to or larger than a threshold value.

In the example shown in FIG. 2, defected regions D20 and D22 are respectively included in the image regions A20 and A22, and defected regions D10, D12, and D14 are included in the non-image region A10 in the inspection image data IMG1.

As shown in FIG. 4, the defected region detection unit 22 calculates a difference between the inspection image data IMG1 and the reference image data REF1 to create the difference image data IMG2. The defected region detection unit 22 detects a difference between the difference image data IMG2 and the reference image data REF1 included in the inspection image data IMG1, and detects, for example, the regions (D10, D12, D14, D20, and D22 in FIGS. 2 to 4) where the difference in color is equal to or larger than the threshold value as the defected region. Both the printing defect and the printing paper defect may be included in the defected region detected by the defected region detection unit 22. Information (for example, position (coordinate), whether the position of the defected region is included in the image region or the non-image region, size (X direction dimension, Y direction dimension, maximum dimension ((X10 and Y10) in FIG. 5, (X12 and Y12) in FIG. 7), minimum dimension), aspect ratio, and color) indicting the defected regions (D10, D12, D14, D20, and D22) detected by the defected region detection unit 22 is sent to the defect determination unit 24.

Information (for example, information indicating whiteness) indicating a color of the printing paper P10 used in the printing apparatus 100 may be included in the reference image data REF1. For example, information based on a measurement method of International Organization for Standardization (ISO) 2470: 1999, Paper, board, and pulps-Measurement of diffuse blue reflectance factor, Japanese Industrial Standards (JIS) P 8148: 2001 may be used as the information indicating the whiteness. In the case, even in a case where the printing paper P10 is paper having low whiteness such as recycled paper, the difference in the color caused by the whiteness of the printing paper P10 can be removed in the difference image data IMG2 by calculating the difference between the inspection image data IMG1 and the reference image data REF1. Thus, it is possible to accurately perform the detection of the defected region.

[Method of Determining Printing Defect and Printing Paper Defect]

Next, a method of determining the printing defect and the printing paper defect will be described. In the following description, the defected regions D10 and D12 are respectively set as the printing defect and the printing paper defect.

Figure 5:
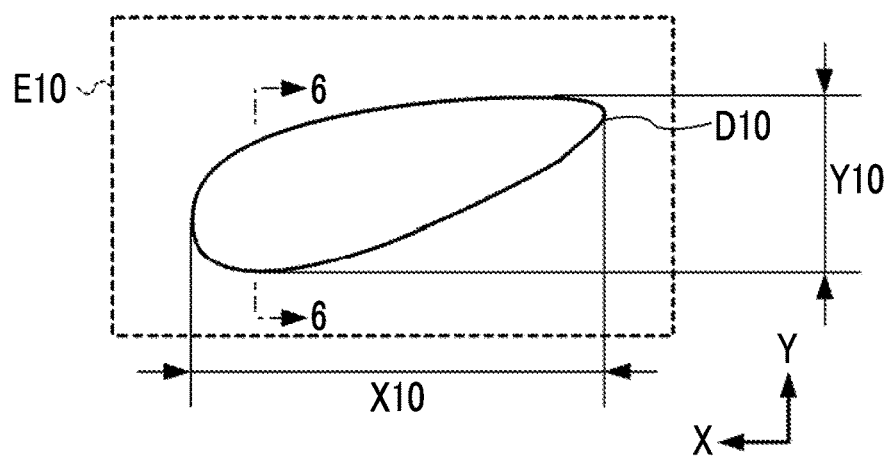
FIG. 5 is a diagram showing an example of a defected region (printing defect).
Figure 6:
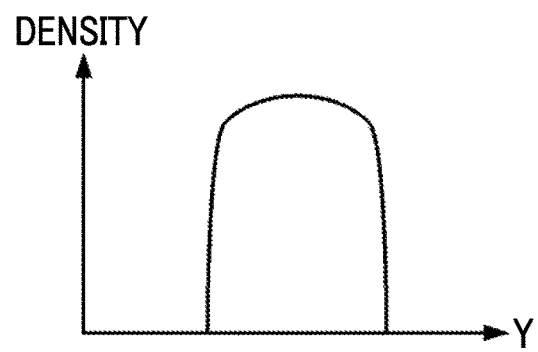
FIG. 6 is a graph showing a density distribution in a region indicated by line 6-6 in FIG. 5.
Figure 7:
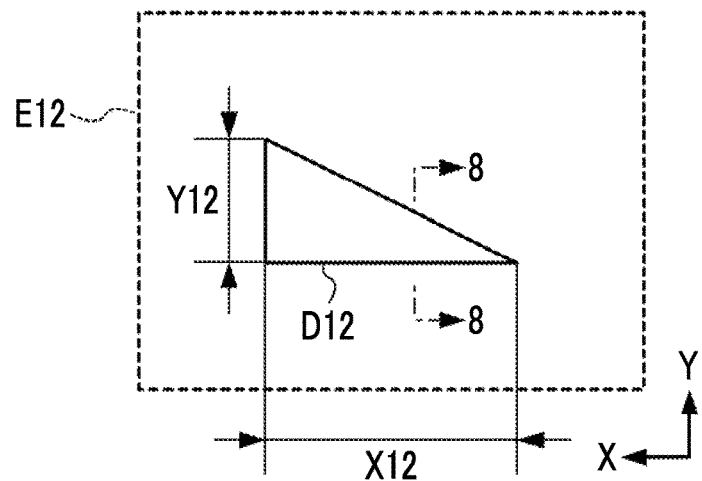
FIG. 7 is a diagram showing an example of a defected region (printing paper defect).
Figure 8:
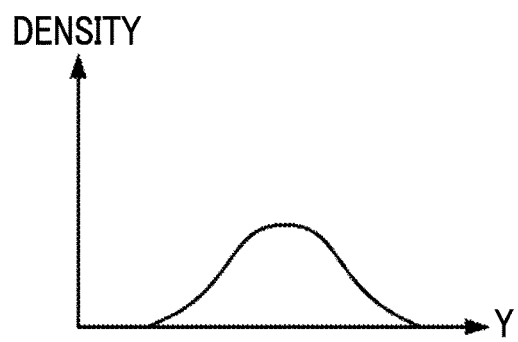
FIG. 8 is a graph showing a density distribution in a region indicated by line 8-8 in FIG. 7.

FIG. 5 is a diagram (enlarged diagram of region E10 in FIG. 4) showing an example of the defected region (printing defect), and FIG. 6 is a graph showing a density distribution in a region indicated by line 6-6 in FIG. 5. FIG. 7 is a diagram (enlarged diagram of region E12 in FIG. 4) showing an example of the defected region (printing paper defect), and FIG. 8 is a graph showing a density distribution in a region indicated by line 8-8 in FIG. 7.

The defect determination unit 24 includes a density determination unit 26 and a color determination unit 28. The defect determination unit 24 determines whether the defected regions D10, D12, and D14 detected from the non-image region A10 among the defected regions detected as described above are the printing defects or the printing paper defects using information relating to the density (color density) and the color. The defect determination unit 24 determines whether the defected regions D20 and D22 included in the image regions A20 and A22 are the printing defects or the printing paper defects based on image feature amount information of the defected region determined as the printing defect in the non-image region A10 and image feature amount information of the defected region determined as the printing paper defect in the non-image region A10.

The density determination unit 26 determines a type of the defect based on a density change amount in the defected region. As shown in FIGS. 5 and 6, in the case of the defected region D10 (printing defect), the density change amount (inclination in the graph in FIG. 6) between the defected region D10 and a region of the peripheral portion thereof is relatively large (steep). On the other hand, as shown in FIGS. 7 and 8, in the case of the defected region D12 (printing paper defect), the density change amount (inclination in the graph in FIG. 8) between the defected region D12 and a region of the peripheral portion thereof is relatively small (gradual). The density determination unit 26 measures the density change amount around the defected region. In a case where the density change amount is equal to or larger than a first threshold value a1, the density determination unit 26 determines that the defected region is the printing defect. In a case where the density change amount is equal to or less than a second threshold value a2 (a2<a1), the density determination unit 26 determines that the defected region is the printing paper defect.

Here, the threshold values a1 and a2 may be predetermined values or may be determined for each lot of the printing paper P10 (product unit on product management of paper) based on a measurement result of the density change amount. For example, a frequency distribution of the measurement result of the density change amount for each defected region of the printing paper P10 may be created, and in a case where two peaks are detected in the frequency distribution of the density change amount, two threshold values may be set based on the peak values.

The color determination unit 28 determines the type of the defect based on a color of the defected region. The printing defect caused by the ink used for printing corresponds to the color of the ink. The color determination unit 28 determines the type of the defect based on a similarity between the color of the defected region and the color of the ink used for the printing.

Specifically, in a case where the color of the ink is set as $(L^*,a^*,b^*)=(L_i^*,a_i^*,b_i^*)$, the color of the defected region is set as $(L^*,a^*,b^*)=(L_p^*,a_p^*,b_p^*)$, and brightness differences $\Delta L^*=L_p^*-L_i^*$, $\Delta a^*=a_p^*-a_i^*$, and $\Delta b^*=b_p^*-b_i^*$ in a Commission Internationale de l'Eclairage (International Commission on Illumination) 1976 L*a*b* color system (CIE), a color difference $\Delta E^*_{ab}$, a chroma difference $\Delta C^*_{ab}$, and a color tone difference $\Delta H^*_{ab}$ are represented by the following equations.

$$\Delta E^*_{ab}=\{(\Delta L^*)^2+(\Delta a^*)^2+(\Delta b^*)^2\}^{1/2}$$

$$\Delta C^*_{ab}=\{(a_p^*)^2+(b_p^*)^2\}^{1/2}-\{(a_i^*)^2+(b_i^*)^2\}^{1/2}$$

$$\Delta H^*_{ab}=\{(\Delta E^*_{ab})^2-(\Delta L^*)^2-(\Delta C^*_{ab})^2\}^{1/2}$$

In a case where values of the color difference $\Delta E^*_{ab}$, the chroma difference $\Delta C^*_{ab}$, and the color tone difference $\Delta H^*_{ab}$ are equal to or less than respective threshold values, the color determination unit 28 determines that the defected region is the printing defect. In a case where the values of the color difference $\Delta E^*_{ab}$, the chroma difference $\Delta C^*_{ab}$, and the color tone difference $\Delta H^*_{ab}$ are not equal to or less than respective threshold values ($\Delta E_{Th}$, $\Delta C_{Th}$, and $\Delta H_{Th}$) (in a case where at least any one value of the color difference $\Delta E^*_{ab}$, the chroma difference $\Delta C^*_{ab}$, or the color tone difference $\Delta H^*_{ab}$ exceeds the threshold value thereof), the color determination unit 28 determines that the defected region is not the printing defect.

In the embodiment, the color difference $\Delta E^*_{ab}$, the chroma difference $\Delta C^*_{ab}$, and the color tone difference $\Delta H^*_{ab}$ are used for determining the type of the defect, but the present invention is not limited thereto. The determination may be performed based on any one of the color difference $\Delta E^*_{ab}$, the chroma difference $\Delta C^*_{ab}$, and the color tone difference $\Delta H^*_{ab}$, or an evaluation value for the determination (evaluation value) may be calculated based on the values of the indices. Another index other than the indices may be used.

The defect determination unit 24 outputs the determination result of the type of the defect based on the density and the color to the paper defect information storage unit 30. Accordingly, paper defect information is stored in the paper defect information storage unit 30.

In the embodiment, there are two threshold values of the density change amount, but may be one threshold value thereof. For example, the density determination unit 26 may determine whether the defected region is the printing paper defect based on the second threshold value a2 (a2<a1), and the color determination unit 28 may determine whether the defected region is the printing defect.

Figure 9:
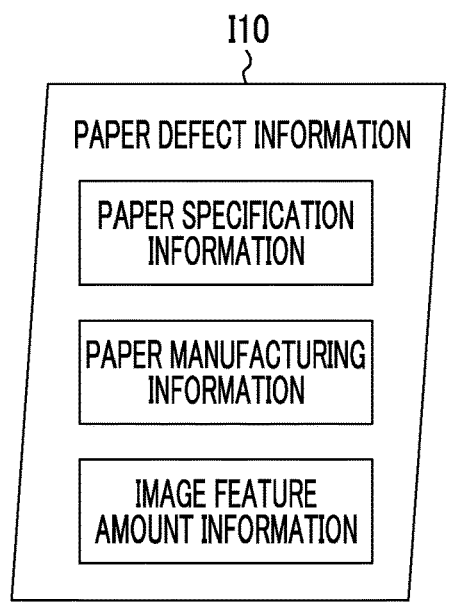
FIG. 9 is a block diagram showing an example of paper defect information.

FIG. 9 is a block diagram showing an example of the paper defect information.

As shown in FIG. 9, paper defect information I10 includes paper specification information, paper manufacturing information, and the image feature amount information.

The paper specification information includes information relating to information (name, brand, manufacturer name, lot number, and the like) for specifying the printing paper P10.

The paper manufacturing information includes a production date, information relating to a paper quality (recycled paper, non-recycled paper), and other pieces of manufacturing information of the printing paper P10.

The image feature amount information includes information relating to respective image feature amounts of the printing defect and the printing paper defect. The image feature amount information includes information, for example, the density change amount and a representative value (average value) thereof of the defected region determined as the printing defect, the density change amount and a representative value (average value) thereof of the defected region determined as the printing paper defect, the indices (color difference $\Delta E^*_{ab}$, chroma difference $\Delta C^*_{ab}$, and color tone difference $\Delta H^*_A$) and representative values (average values) thereof relating to the color of the defected region determined as the printing defect, and the aspect ratio.

The image feature amount information may include only the information relating to the image feature amount of the printing paper defect.

Figure 10:
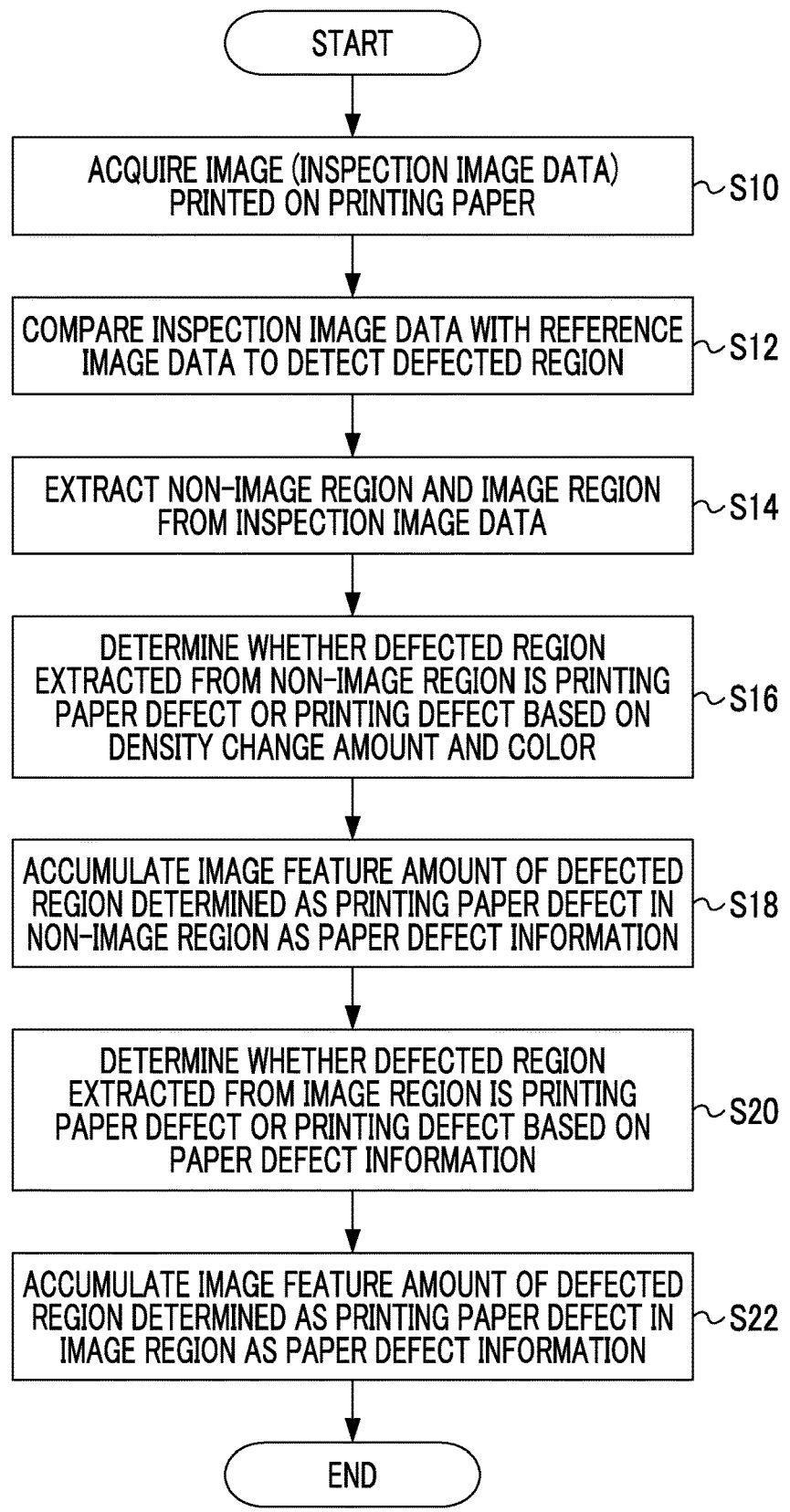
FIG. 10 is a flowchart showing a method of inspecting a printing result according to the embodiment of the present invention.
Figure 11:
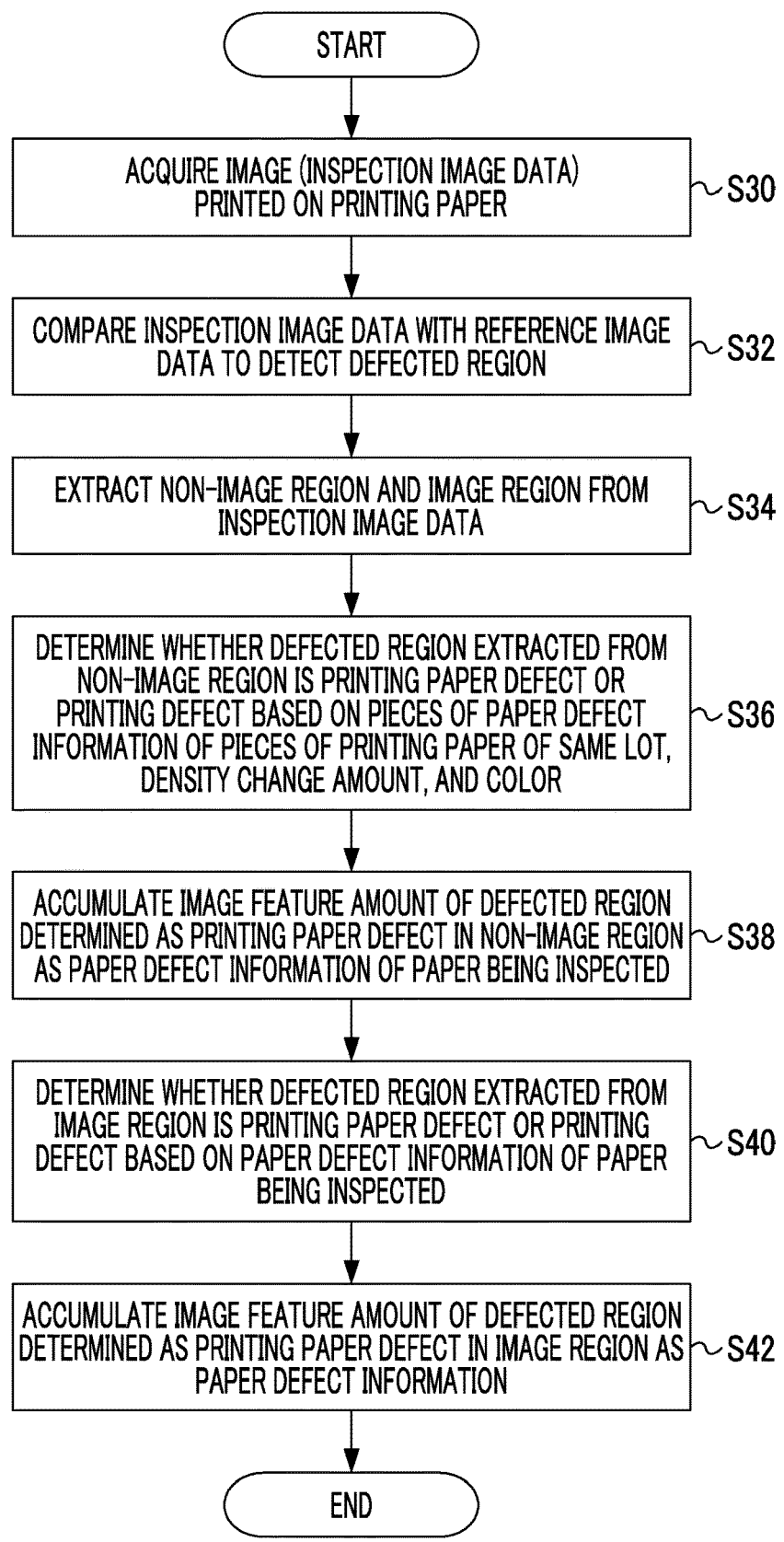
FIG. 11 is a flowchart showing a method of inspecting a printing result using paper defect information according to the embodiment of the present invention.

The defect determination unit 24 can perform the determination of the types of the defected regions included in the image regions A20 and A22 using the image feature amount information (refer to FIGS. 10 and 11). Specifically, the threshold values a1 and a2 of the density change amount used for the determination based on the density change amounts in the image regions A20 and A22 can be respectively determined based on the density change amount and the representative value (average value) thereof of the defected region determined as the printing defect, the density change amount and the representative value (average value) thereof of the defected region determined as the printing paper defect in the non-image region A10. The threshold values ($\Delta E_{Th}$, $\Delta C_{th}$, and $\Delta H_{Th}$) used for the determination of the color determination unit 28 in the image regions A20 and A22 can be determined based on the indices (color difference $\Delta E^*_{ab}$, chroma difference $\Delta C^*_{ab}$, and color tone difference $\Delta H^*_{ab}$) and the representative values (average values) thereof relating to the color of the defected region determined as the printing defect in the non-image region A10. The defect determination unit 24 can perform the determination of the types of the defects in the image regions A20 and A22 using the threshold values.

In the embodiment, the threshold values for the density change amount and the indices of the color are set using the paper defect information relating to the determination result of the type of the defected region in the non-image region, but the present invention is not limited thereto. For example, the determination may be performed using morphological features (shape, size, aspect ratio, and the like) of the printing paper defect or a feature relating to a color change included in the paper defect information in addition to the determination based on the density change amount and the color.

In a case of pieces of printing paper of the same lot, the same brand, and close manufacturing dates or pieces of printing paper of the same manufacturer, it is considered that some of the raw materials of the pieces of printing paper are common. Therefore, it is considered that types and sizes of the foreign substances mixed into the pieces of printing paper through the raw materials are similar or the color changes of the pieces of printing paper caused by the foreign substances are similar. Consequently, it is possible to more appropriately perform the determination of the printing paper defect according to the characteristics of the printing paper P10 by performing the determination using the morphological features (shape, size, aspect ratio, and the like) of the printing paper defect or the feature relating to the color change included in the paper defect information having paper specification information similar to the printing paper P10 to be inspected.

In the embodiment, the type of the defected region is determined based on the density change amount and the color, but the present invention is not limited thereto. For example, a determination algorithm by machine learning may be constructed based on information on the accumulated image feature amount. An evaluation value for a comprehensive evaluation may be calculated based on a comparison result of the density change amount and each index of the color with each threshold value thereof, and the determination may be performed using the evaluation value for the comprehensive evaluation. For example, an approximation degree of the density change amount and the index of the color to each threshold value may be calculated, and the evaluation value for the comprehensive evaluation (comprehensive evaluation value) may be calculated according to the approximation degree (evaluation value indicating that the defect is the printing defect may be decreased as the index of the color is a value close to the threshold value, and evaluation value indicating that the defect is the printing defect may be increased as the difference between the index of the color and the threshold value increases).

In calculating the evaluation value for the comprehensive evaluation, information relating to the aspect ratio of the defected region may be added. For example, in a case where the defected region extends along the transportation direction (X direction) of the printing paper P10, since it is estimated that the ink dripping spreads along the transportation direction of the printing paper P10, the evaluation value indicating that the defect is the printing defect caused by the ink may be increased.

[Method of Inspecting Printing Result]

FIG. 10 is a flowchart showing a method of inspecting a printing result according to the embodiment of the present invention.

First, the image data acquisition unit 18 of the printing result inspection apparatus 10 acquires an image (inspection image data IMG1) obtained by imaging the printing paper P10 from the camera 50 (step S10: inspection image data acquisition step).

Next, the defected region detection unit 22 compares the inspection image data IMG1 with the reference image data REF1 used for printing the printing paper P10 to detect the defected regions D10, D12, D14, D20, and D22 (step S12: defected region detection step). The defected region detection unit 22 extracts the non-image region A10 and the image regions A20 and A22 from the inspection image data IMG1 based on a dropping region of the ink, that is, density of a region where an image is present in an image forming region (step S14).

The defect determination unit 24 determines whether the defected regions D10, D12, and D14 extracted from the non-image region A10 are the printing defect or the printing paper defect based on the density change amount and the color (step S16: first defect determination step), and the image feature amount of the defected region determined as the printing paper defect in the non-image region A10 is stored in the paper defect information I10 and is accumulated in the paper defect information storage unit 30 (step S18: storage step).

Next, the defect determination unit 24 determines whether the defected regions D20 and D22 extracted from the image regions A20 and A22 are the printing defect or the printing paper defect based on the paper defect information I10 (step S20: second defect determination step).

The image feature amounts of the defected regions determined as the printing paper defect in the image regions A20 and A22 are stored in the paper defect information I10 and are accumulated in the paper defect information storage unit 30 (step S22).

[Method of Inspecting Printing Result Using Paper Defect Information]

FIG. 11 is a flowchart showing a method of inspecting a printing result using paper defect information according to the embodiment of the present invention.

First, the image data acquisition unit 18 of the printing result inspection apparatus 10 acquires an image (inspection image data IMG1) obtained by imaging the printing paper P10 from the camera 50 (step S30).

Next, the defected region detection unit 22 compares the inspection image data IMG1 with the reference image data REF1 used for printing the printing paper P10 to detect the defected regions D10, D12, D14, D20, and D22 (step S32). The defected region detection unit 22 extracts the non-image region A10 and the image regions A20 and A22 from the inspection image data IMG1 based on the dropping region of the ink, that is, density of a region where an image is present in an image forming region (step S34).

The defect determination unit 24 acquires pieces of paper defect information of pieces of printing paper in which some (the same lot) of the pieces of paper specification information is common, and determines whether the defected regions D10, D12, and D14 extracted from the non-image region A10 are the printing defect or the printing paper defect based on the pieces of paper defect information, the density change amount, and the color (step S36). The image feature amount of the defected region determined as the printing paper defect in the non-image region A10 is stored in the paper defect information HO and is accumulated in the paper defect information storage unit 30 (step S38).

Next, the defect determination unit 24 determines whether the defected regions D20 and D22 extracted from the image regions A20 and A22 are the printing defect or the printing paper defect based on the paper defect information I10 (step S40).

The image feature amounts of the defected regions determined as the printing paper defect in the image regions A20 and A22 are stored in the paper defect information I10 and are accumulated in the paper defect information storage unit 30 (step S42).

The present invention can be also realized as a program (printing result inspection program) that causes a computer to realize the processes described above, or a non-transitory recording medium or a program product storing the program. It is possible to cause calculation means, recording means, and the like of the computer to function as an inspection image data acquisition function, a defected region detection function, a first defect determination function, a storage function, and a second defect determination function of the printing result inspection program by employing the printing result inspection program in the computer.

EXPLANATION OF REFERENCES

10: printing result inspection apparatus
12: control unit
14: operation unit
16: display unit
18: image data acquisition unit
20: reference image data storage unit
22: defected region detection unit
24: defect determination unit
26: density determination unit
28: color determination unit
30: paper defect information storage unit
50: camera
100: printing apparatus
P10: printing paper
A10, A12: non-image region
A20: image region
D10, D12, D14, D20, D22: defected region
IMG1: inspection image data
IMG2: difference image data
REF1: reference image data
T10: transportation path
I10: paper defect information
S10 to S22: each step of a method of inspecting a printing result
S30 to S42: each step of a method of inspecting a printing result using paper defect information

What is claimed is:

1. A printing result inspection apparatus comprising:
inspection image data acquisition means for acquiring inspection image data obtained by imaging printing paper after printing;
defected region detection means for comparing the inspection image data with reference image data including an image printed on the printing paper to detect a defected region from the inspection image data;
first defect determination means for determining whether the defected region included in a non-image region is a printing defect caused by a printing step or a printing paper defect caused by printing paper based on a density change amount and a color of the defected region included in the non-image region where the image on the printing paper is not printed among defected regions detected by the defected region detection means;
storage means for storing image feature amount information indicating an image feature amount of the defected region determined as the printing paper defect by the first defect determination means; and
second defect determination means for determining whether the defected region included in an image region excluding the non-image region on the printing paper among the defected regions detected by the defected region detection means is the printing defect or the printing paper defect based on the image feature amount information of the defected region determined as the printing paper defect, and a density change amount and a color of the defected region included in the image region.

2. The printing result inspection apparatus according to claim 1,
wherein the storage means stores image feature amount information indicating an image feature amount of a defected region determined as the printing paper defect by the second defect determination means.

3. The printing result inspection apparatus according to claim 1, wherein the storage means stores paper specification information that specifies the printing paper in correlation with the image feature amount information, and wherein in a case of inspecting printing paper having the same paper specification information as paper specification information recorded in the storage means, the first defect determination means and the second defect determination means determine whether the defected region is the printing defect or the printing paper defect using the image feature amount information correlated with the paper specification information.

4. The printing result inspection apparatus according to claim 1, wherein the storage means stores image feature amount information indicating an image feature amount of the defected region determined as the printing defect by the first defect determination means, and wherein the second defect determination means determines whether the defected region included in the image region excluding the non-image region on the printing paper is the printing defect or the printing paper defect based on the image feature amount information of the defected region determined as the printing paper defect, the image feature amount information of the defected region determined as the printing defect, and the density change amount and the color of the defected region included in the image region.

5. The printing result inspection apparatus according to claim 1, wherein in a case where the density change amount measured for the defected region is equal to or larger than a first threshold value, the first defect determination means determines that the defected region is the printing defect.

6. The printing result inspection apparatus according to claim 5, wherein in the case where the density change amount measured for the defected region is equal to or larger than the first threshold value, the first defect determination means determines that the defected region is the printing defect, and in a case where the density change amount measured for the defected region is equal to or less than a second threshold value which is smaller than the first threshold value, the first defect determination means determines that the defected region is the printing paper defect.

7. The printing result inspection apparatus according to claim 1, wherein in a case where a color of an ink used for printing the printing paper and a color of the defected region are compared with each other, and the color of the ink and the color of the defected region are determined to be the same, the first defect determination means determines that the defected region is the printing defect.

8. The printing result inspection apparatus according to claim 7, wherein the first defect determination means determines whether the defected region is the printing defect based on at least one of a color difference, a chroma difference, or a color tone difference between the color of the ink used for printing the printing paper and the color of the defected region.

9. The printing result inspection apparatus according to claim 1, wherein in a case where there is the defected region which is not possible to be determined as either the printing defect or the printing paper defect, the first defect determination means calculates a comprehensive evaluation value based on the density change amount and the color of the defected region and determines whether the defected region is the printing defect or the printing paper defect based on the comprehensive evaluation value.

10. The printing result inspection apparatus according to claim 9, wherein the first defect determination means calculates the comprehensive evaluation value based on a shape of the defected region.

11. The printing result inspection apparatus according to claim 1, wherein the reference image data includes information indicating a color of the printing paper, and wherein the defected region detection means calculates a difference between the inspection image data and the reference image data and the color of the printing paper, and acquires difference image data to detect the defected region from the inspection image data.

12. A method of inspecting a printing result comprising:

an inspection image data acquisition step of acquiring inspection image data obtained by imaging printing paper after printing;

a defected region detection step of comparing the inspection image data with reference image data including an image printed on the printing paper to detect a defected region from the inspection image data;

a first defect determination step of determining whether the defected region included in a non-image region is a printing defect caused by a printing step or a printing paper defect caused by printing paper based on a density change amount and a color of the defected region included in the non-image region where the image on the printing paper is not printed among defected regions detected in the defected region detection step;

a storage step of storing image feature amount information indicating an image feature amount of the defected region determined as the printing paper defect in the first defect determination step in storage means; and a second defect determination step of determining whether the defected region included in an image region excluding the non-image region on the printing paper among the defected regions detected in the defected region detection step is the printing defect or the printing paper defect based on the image feature amount information of the defected region determined as the printing paper defect, and a density change amount and a color of the defected region included in the image region.

13. A non-transitory computer-readable recording medium that stores a printing result inspection program to cause a computer to execute:

an inspection image data acquisition function of acquiring inspection image data obtained by imaging printing paper after printing;

a defected region detection function of comparing the inspection image data with reference image data including an image printed on the printing paper to detect the defected region from the inspection image data;

a first defect determination function of determining whether a defected region included in a non-image region is a printing defect caused by a printing step or a printing paper defect caused by printing paper based on a density change amount and a color of the defected region included in the non-image region where the image on the printing paper is not printed among defected regions detected by the defected region detection function;
a storage function of storing image feature amount information indicating an image feature amount of the defected region determined as the printing paper defect by the first defect determination function; and
a second defect determination function of determining whether the defected region included in an image region excluding the non-image region on the printing paper among the defected regions detected by the defected region detection function is the printing defect or the printing paper defect based on the image feature amount information of the defected region determined as the printing paper defect, and a density change amount and a color of the defected region included in the image region.

* * * * *